United States Patent [19]

Lesher et al.

[11] 4,271,168

[45] Jun. 2, 1981

[54] SELECTED 3-ACYLAMINO-5-[4(OR 3)-PYRIDINYL]-2(1H)-PYRIDINONES

[75] Inventors: George Y. Lesher; Chester J. Opalka, Jr., both of Rensselaer, N.Y.

[73] Assignee: Sterling Drug Inc., New York, N.Y.

[21] Appl. No.: 106,764

[22] Filed: Dec. 26, 1979

[51] Int. Cl.³ .................... A61K 31/44; C07D 213/57
[52] U.S. Cl. ...................................... 424/263; 546/257
[58] Field of Search .......................... 424/263; 546/257

[56] References Cited

U.S. PATENT DOCUMENTS

| | | | |
|---|---|---|---|
| 4,004,012 | 1/1977 | Lesher et al. .................... | 546/257 X |
| 4,072,746 | 2/1978 | Lesher et al. ................. | 424/263 OR |
| 4,107,315 | 8/1978 | Lesher et al. ................. | 424/263 OR |

*Primary Examiner*—John D. Randolph
*Attorney, Agent, or Firm*—Robert K. Bair; B. Woodrow Wyatt

[57] ABSTRACT

3-Acylamino-5-[4(or 3)-pyridinyl]-2(1H)-pyridinones or pharmaceutically-acceptable acid-addition salts thereof useful as cardiotonic agents are prepared by reacting the corresponding 3-amino compound with an acylating agent providing acyl, where acyl is 2-acetoxypropanoyl, acetoacetyl or acetoxyacetyl. Cardiotonic compositions and method for increasing cardiac contractility using said 3-acylamino compounds as active component are disclosed.

10 Claims, No Drawings

SELECTED 3-ACYLAMINO-5-[4(OR 3)-PYRIDINYL]-2(1H)-PYRIDINONES

BACKGROUND OF THE INVENTION

1. Field of the Invention

This invention relates to selected 3-acylamino-5-(pyridinyl)-2(1H)-pyridinones, useful as cardiotonic agents, and to their preparation.

2. Description of the Prior Art

Lesher and Opalka U.S. Pat. Nos. 4,004,012, issued Jan. 18, 1977, and 4,072,746, issued Feb. 7, 1978, show as cardiotonic agents 3-amino-5-(pyridinyl)-2(1H)-pyridinones and their corresponding 3-(lower-alkanoylamino)-5-(pyridinyl)-2(1H)-pyridinones derivatives, which are prepared by reacting said 3-amino compound with a lower-alkanoylating agent.

SUMMARY OF THE INVENTION

In a composition aspect, the invention relates to 3-acylamino-5-[4(or 3)-pyridinyl]-2(1H)-pyridinone or pharmaceutically-acceptable acid-addition salt thereof, where acyl is 2-acetoxypropanoyl, acetoacetyl or acetoxyacetyl, which is useful as a cardiotonic agent.

The invention is a process aspect resides in process of producing 3-acylamino-[4(or 3)-pyridinyl]-2(1H)-pyridinones which comprises reacting 3-amino-5-[4(or 3)-pyridinyl]-2(1H)-pyridinone with an acylating agent, where acyl is 2-acetoxypropanoyl, acetoacetyl or acetoxyacetyl.

Another composition aspect of the invention relates to a cardiotonic composition for increasing cardiac contractility in a patient, said composition comprising a pharmaceutically-acceptable carrier and, as the active component thereof, the cardiotonic 3-acylamino-5-[4(or 3)-pyridinyl]-2(1H)-pyridinone or pharmaceutically-acceptable acid-addition salt thereof, where acyl is 2-acetoxypropanoyl, acetoacetyl or acetoxyacetyl.

In a method aspect, the invention relates to a method for increasing cardiac contractility in a patient requiring such treatment which comprises the administration of a medicament comprising a pharmaceutically-acceptable carrier and, as the active component thereof, the cardiotonic 3-acylamino-5-[4-(or 3)pyridinyl]-(1H)-pyridinone or pharmaceutically-acceptable acid-addition salt thereof, where acyl is 2-acetoxypropanoyl, acetoacetyl or acetoxyacetyl.

DETAILED DESCRIPTION INCLUSIVE OF PREFERRED EMBODIMENTS

In a composition aspect the invention resides in 3-acylamino-5-[4-(or 3)-pyridinyl]-2(1H)-pyridinone or pharmaceutically-acceptable acid-addition salt thereof, where acyl is 2-acetoxypropanoyl, acetoacetyl or acetoxyacetyl. These compounds are useful as cardiotonic agents, as determined by standard pharmacological evaluation procedures. Preferred embodiments are the above compounds where acyl is 2-acetoxypropanoyl and acetoacetyl.

In a process aspect the invention resides in the process of reacting 3-amino-5-[4-(or 3)-pyridinyl]-2(1H)pyridinone with an acylating agent providing acyl to produce 3-acylamino-5-[4-(or 3)-pyridinyl]-2(1H)-pyridinone where acyl is 2-acetoxypropanoyl, acetoacetyl, or acetoxyacetyl.

Another composition aspect of the invention resides in a cardiotonic composition for increasing cardiac contractility, said composition comprising a pharmaceutically-acceptable carrier and, as the active component thereof, a cardiotonic 3-acylamino-5-[4(or 3)-pyridinyl]-2(1H)-pyridinone or pharmaceutically-acceptable acid-addition salt thereof, where acyl is 2-acetoxypropanoyl, acetoacetyl or acetoxyacetyl.

A method aspect of the invention resides in the method for increasing cardiac contractility in a patient requiring such treatment which comprises administering to such patient an effective amount of a cardiotonic 3-acylamino-5-[4(or 3)-pyridinyl]-2(1H)-pyridinone or pharmaceutically-acceptable acid-addition salt thereof, where acyl is 2-acetoxypropanoyl, acetoacetyl or acetoxyacetyl.

The 3-acylamino-5-[4(or 3)-pyridinyl]2(1H)-pyridinones of the invention are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it was convenient to use the hydrochloride. However, other appropriate pharmaceutically-acceptable salts within the scope of the invention are those derived from mineral acids such as sulfuric acid, phosphoric acid and sulfamic acid; and organic acid such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the sulfate, phosphate, sulfamate, acetate, citrate, lactate, tartrate, methanesulfonate, ethanesulfonate, benzenesulfonate, p-toluenesulfonate, cyclohexylsulfamate and quinate respectively.

The acid-addition salts of said basic compounds of the invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structures of the compounds of the invention were assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same, as follows.

A preferred aspect of acylating 3-amino-5-[4(or 3)-pyridinyl]-2(1H)-pyridinone is carried out by treating at room temperature, i.e., about 20° to 30° C., the 3-amino compound with the appropriate acyl halide, preferably 2-acetoxypropanoyl chloride, acetoacetyl chloride or acetoxyacetyl chloride, in pyridine. A preferred aspect of acylating with an acetoacetylating agent is carried out by reacting the 3-amino compound with diketene in a suitable aprotic solvent, preferably tetrahydrofuran; the reaction is preferably carried out by mixing the reactants chilled in an ice bath and then heating the reaction mixture on a steam bath.

The following examples will further illustrate the invention without, however, limiting it thereto.

EXAMPLE 1

3-[2-(Acetoxy)propanoylamino]-5-(4-pyridinyl-2(1H)-pyridinone

To a stirred slurry containing 18.7 g. of 3-amino-5-(4-pyridinyl)-2(1H)-pyridinone and 300 ml. of pyridine at room temperature was added dropwise over a period of about 1 hour 16.5 g. of 2-acetoxypropanoyl chloride and the resulting mixture was cooled in an ice bath. The product that separated was collected, washed with ether, dried, recrystallized from methanol, washed successively with ethanol and ether and dried to yield as a pale yellow solid 12.5 g. of 3-[2-(acetoxy)propanoylamino]-5-(4-pyridinyl-2(1H)-pyridinone hydrochloride, m.p. 294°–295° C. with decomposition.

EXAMPLE 2

3-(Acetoacetylamino)-5-(4-pyridinyl)-2(1H)-pyridinone, alternatively named N-(1,6-dihydro-6-oxo-[3,4'-bipyridin]-5-yl)-3-oxobutanamide To a stirred suspension containing 9.4 g. of 3-amino-5-(4-pyridinyl)-2(1H)-pyridinone suspended in 250 ml. of tetrahydrofuran chilled in an ice bath was added dropwise over a period of 5 minutes 6.3 g. of diketene and the resulting mixture was stirred for an additional 10 minutes while cold. The ice bath was replaced with a steam bath and the reaction mixture was refluxed gently with stirring for 1 hour. The reaction mixture was then cooled and the separated solid was collected, washed well with ether and air-dried to give 12.1 g. of 3-(acetoacetylamino)-5-(4-pyridinyl)-2(1H)-pyridinone, m.p. 208°–210° C. with the composition.

Acid-addition salts of 3-(acetoacetylamino)-5-(4-pyridinyl)-2(1H)-pyridinone are conveniently prepared by adding to a mixture of 0.5 g. of 3-acetoacetylamino)-5-(4-pyridinyl)-2(1H)-pyridinone in about 10 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulphate, phosphate, respectively. Also, the acid-addition salt is conveniently prepared in aqueous solution by adding to water with stirring molar equivalent quantities of 3-(acetoacetylamino)-5-(4-pyridinyl)-2(1H)-pyridinone and the appropriate acid, e.g., lactic acid or hydrochloric acid, to prepare respectively the lactate or hydrochloride salt of 3-(acetoacetylamino)-5-(4-pyridinyl)-2(1H)-pyridinone in aqueous solution.

EXAMPLE 3

3-(2-acetoxypropanoylamino)-5-(3-pyridinyl)-2(1H)-pyridinone

Following the procedure described in Example 1 but using a molar equivalent quantity of 3-amino-5-(3-pyridinyl)-2(1H)-pyridinone in place of 3-amino-5-(4-pyridinyl)-2(1H)-pyridinone, it is contemplated that the corresponding 3-(2-acetoxypropanoylamino)-5-(3-pyridinyl)-2(1H)-pyridinone can be obtained.

EXAMPLE 4

3-(Acetoacetylamino)-5-(3-pyridinyl)-(1H)-pyridinone

Following the procedures described in Example 2 but using a molar equivalent quantity of 3-amino-5-(3-pyridinyl)-2(1H)-pyridinone in place of 3-amino-5-(4-pyridinyl)-(1H)-pyridinone, it is contemplated that the corresponding 3-(acetoacetylamino)-5-(3-pyridinyl)-(1H)-pyridinone can be obtained.

EXAMPLE 5

3-(Acetoxyacetylamino)-5-(4-pyridinyl)-2(1H)-pyridinone

To a stirred mixture containing 9.35 g. of 3-amino-5-(4-pyridinyl)-2(1H)-pyridinone and 100 ml. of dried pyridine under an atmosphere of nitrogen (bubbled slowly through the reaction mixture) was added dropwise with stirring over a period of about 8 minutes 8.22 g. of acetoxyacetyl chloride whereupon the reaction temperature rose from 22° to 44° C. The reaction mixture was stirred for 2 and ½ hours and was allowed to stand at room temperature overnight under nitrogen. To the reaction mixture was added acetone (200 ml.) and the mixture stirred well. The separated solid was collected, washed with acetone, air-dried, and then dried in vacuo at 80° C. to yield 16.3 g. of the crude product as its hydrochloride salt. A 6.5 g. portion of product was dissolved in hot acetic acid to which was added a small amount of hydrogen chloride in ethanol (aided dissolution). The hot solution was treated with decolorizing charcoal, filtered to give a bright yellow filtrate from which crystals separated. The mixture was allowed to cool to room temperature and stand overnight. The crystalline precipitate was collected, washed with acetone and dried in vacuo at 90° C. for about 40 hours to yield 5.2 g. of 3-(acetoxyacetylamino)-5-(4-pyridinyl)-2(1H)-pyridinone as its monohydrochloride hemiacetate, m.p. 267°–290° C. with decomposition.

The compound of Example 6 hereinbelow is presented for comparative purposes. The novel product of this example, which is not part of the instant invention herein claimed, does have low cardiotonic activity at the highest dose used in the cat atria test procedure described below; however its cardiotonic activity is significantly less than that found for the compounds of the invention.

EXAMPLE 6

3-(Hydroxyacetylamino)-5-(4-pyridinyl)-2(1H)-pyridinone

A mixture containing 6.5 g. of 3-acetoxyacetylamino)-5-(4-pyridinyl)-2(1H)-pyridinone and 50 ml. of concentrated aqueous ammonia was stirred for 3 hours at room temperature. The resulting clear solution was diluted with water and the resulting solution was cooled overnight. The solution was then heated in vacuo on a steam bath to remove part of the water. After partial removal of the water (about 100 ml. of solution remaining), a heavy yellow precipitate formed. The mixture was cooled and the separated product was collected, washed with cold water and air dried to yield 4.6 g. of the crude product. This material was combined with another 1.4 g. of crude product prepared in another run and the resulting 6.0 g. was recrystallized from methanol (750 ml.), washed with cold methanol and dried at 80°–85° C. in vacuo to yield 4.55 g. of 3-(hydroxyacetylamino)-5-(4-pyridinyl)-2(1H)-pyridinone, m.p. 271°–274° C. with decomposition.

The usefulness of the compounds of the invention as cardiotonic agents is demonstrated by their effectiveness in standard pharmacological test procedures, for example, in causing a significant increase in the contractile force of the isolated cat atria and papillary muscle and in causing a significant increase in the cardiac contractile force in the anesthetized dog with low or minimal changes in heart rate and blood pressure. These known test procedures have been described, e.g., in U.S. Pat. No. 4,072,746, issued Feb. 7, 1978.

When tested by said isolated cat atria and papillary muscle procedure, the compounds of the invention when tested at doses of 100 μg./ml., were found to cause significant increase, that is, greater than 25%, in papillary muscle force and a significant increase, that is, greater than 25%, in right atrial force, while causing a lower percentage increase per dose in right atrial rate than the percentage increase in right atrial or papillary muscle force. Preferred embodiments, i.e., the compounds of Examples 1 and 2, when tested at 30 μg./ml. by this procedure each were found to cause a papillary muscle force increase of about 34–35%. In contrast, the compound of Example 6 when tested by this procedure was found to be inactive at 30 μg./ml. and to cause only a papillary muscle force increase of about 18% at a dose of 100 μg./ml. compared with 71% and 185% respectively for the compounds of Example 1 and 2, and 57% for the compound of Example 5.

When tested by the anesthetized dog procedure, the preferred embodiments of Examples 1 and 2 when administered intravenously at a dose of 3.0 and 10.0 mg./kg. caused a significant increase, that is, greater than 25%, in cardiac contractile force or cardiac contractility with only low or minimal changes in heart rate and blood pressure.

The present invention includes within its scope a cardiotonic composition for increasing cardiac contractility, said composition comprising a pharmaceutically-acceptable carrier and, as the active component thereof, the cardiotonic 3-acylamino-5-[4-(or 3)-pyridinyl]-2(1H)-pyridinone (where acyl is as defined above) or pharmaceutically-acceptable acid-addition salt thereof. The invention also includes within its scope the method for increasing cardiac contractility in a patient requiring such treatment which comprises administering to such patient an effective amount of said 3-acylamino-5-[4(or 3)-pyridinyl]-2(1H)-pyridinone or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavouring, perfuming and preserving agents. According to the the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, perserving, wetting, emulsifying and dispersing agents.

They may be sterilized, for example by filtration through a bacteria-retaining filter, by incorporation of sterilising agents in the composition, by irradiation or by heating. They may also be manufactured in the form of sterile solid compositions which can be dissolved in sterile water or some other sterile injectable medium immediately before use.

The percentages of active component in the said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. 3-Acylamino-5-[4-(or 3)-pyridinyl]-2(1H)-pyridinone, where acyl is 2-acetoxypropanoyl, acetoacetyl or acetoxyacetyl, or pharmaceutically-acceptable acid-addition salt thereof.

2. A compound according to claim 1 where acyl is 2-acetoxypropanoyl.

3. A compound according to claim 1 where acyl is acetoacetyl.

4. A compound according to claim 1 where acyl is acetoxyacetyl.

5. A cardiotonic composition for increasing cardiac contractility, said composition comprising a pharmaceutically-acceptable inert carrier and, as the active component thereof, an effective amount of a cardiotonic 3-acylamino-5-[4(or 3)-pyridinyl]-2(1H)-pyridinone, where acyl is 2-acetoxypropanoyl, acetoacetyl or acetoxyacetyl, or pharmaceutically-acceptable acid-addition salt thereof.

6. A composition according to claim 5 where the active component is 3-(2-acetoxypropanoylamino)-5-(4-pyridinyl)-2(1H)-pyridinone or pharmaceutically-acceptable acid-addition salt thereof.

7. A composition according to claim 5 where the active component is 3-(acetoacetylamino)-5-(4- pyridinyl)-2(1H)-pyridinone or pharmaceutically-acceptable acid-addition salt thereof.

8. The method for increasing cardiac contractility in a patient requiring such treatment which comprises administering orally or parenterally in a solid or liquid dosage form to such patient an effective amount of a cardiotonic 3-acylamino-5-[4(or 3)-pyridinyl]-2(1H)-pyridinone, where acyl is 2-acetoxypropanoyl, acetoacetyl or acetoxyacetyl, or pharmaceutically-acceptable acid-addition salt thereof.

9. The method according to claim 8 where acyl is 2-acetoxypropanoyl.

10. The method according to claim 8 where acyl is acetoacetyl.

* * * * *